United States Patent [19]

Piperato

[11] Patent Number: 4,862,772
[45] Date of Patent: Sep. 5, 1989

[54] TAMPERPROOF, SINGLE USE, DISPOSABLE TATTOO EQUIPMENT

[76] Inventor: Richard A. Piperato, 363 Portia St., South Amboy, N.J. 08879

[21] Appl. No.: 288,448

[22] Filed: Dec. 22, 1988

[51] Int. Cl.$^4$ ............................................. A61B 17/20
[52] U.S. Cl. ................................... 81/9.22; 206/363; 206/367; 604/110
[58] Field of Search .................. 81/9.22, 9.2; 604/110, 604/111, 192, 263; 206/363, 367, 438

[56] References Cited

U.S. PATENT DOCUMENTS

| | | | |
|---|---|---|---|
| 464,801 | 12/1891 | O'Reilly | 81/9.22 |
| 473,207 | 4/1892 | Carey | 81/9.22 |
| 4,159,659 | 7/1979 | Nightingale | 81/9.22 |
| 4,170,234 | 10/1979 | Graham | 206/363 |
| 4,538,612 | 9/1985 | Patrick, Jr. | 206/363 |
| 4,582,060 | 4/1986 | Bailey | 81/9.22 |
| 4,592,744 | 6/1986 | Jagger et al. | 604/192 |
| 4,771,660 | 9/1988 | Yacowitz | 81/9.22 |

*Primary Examiner*—Roscoe V. Parker
*Attorney, Agent, or Firm*—Richard C. Litman

[57] ABSTRACT

A tattoo needle bar holder and needle bar assembly is fashioned so as to be economical to manufacture and therefore readily disposable in order to promote sanitary conditions in the tattoo industry. The needle bar holder is preferably formed from a plastic material in order to render it incapable of withstanding sterilization processes involving very high pressure and temperatures, which would render the holder incapable of further use. The material is preferably also stained by the inks normally used in the industry, thereby serving to alert persons of any prior use. The caps which seal the assembly prior to use are preferably formed to require the breakage of a frangible portion upon removal in order to prevent the reinstallation of the caps. The needle bar assembly is composed of several relatively simple components for ease of manufacture, and contains an eye and plastic or elastomer grommet at the upper end of the needle bar for precise attachment to the tattooing mechanism. The grommet is also of a material which would be damaged under conditions of extreme pressure and/or temperature, thereby rendering the needle bar assembly to which it is attached incapable of further use if sterilization is attempted.

8 Claims, 1 Drawing Sheet

TAMPERPROOF, SINGLE USE, DISPOSABLE TATTOO EQUIPMENT

FIELD OF THE INVENTION

This invention relates generally to improvements in the art of tattooing, and more specifically to disposable tattoo equipment intended for a single use combined with a sterile tamperproof container serving as a portion of the equipment.

BACKGROUND OF THE INVENTION

The art of tattooing has been known for a considerable period of time. Patents exist for tattooing apparatus predating this application by nearly a century; O'Reilly U.S. Patent No. 464,801 is an example. Only relatively recently, however, has it become recognized that tattooing may also be a source of disease through the use of unsterile equipment. The tattooing process has since become recognized as a vehicle for the spread of such diseases as serum hepatitis, and even more recently, acquired immune deficiency syndrome, or AIDS.

The tattooing industry has suffered as a result of such discoveries, and although the vast majority of the industry attempts to provide sterile equipment, such equipment is complex and therefore difficult to sterilize. No patents of which the inventor is aware directly address this problem. While present equipment may be disposed of after a single use, thereby precluding any problems involving sterilization, the present materials and construction of such equipment make such a practice prohibitively costly. The need arises for relatively economical tattooing equipment which is assured to be sterile prior to use by means of sealed containers and holders, and materials and construction of which require disposal after a single use.

DESCRIPTION OF THE RELATED ART

Needle bar holders and needle assemblies patterned similarly to the present invention have been disclosed in various patents. Nightingale U.S. Pat. No. 4,159,659 discloses an actuating mechanism as well as a needle bar holder much like that of the present invention. The holder, however, is made and intended for use primarily with the accompanying actuating mechanism, and further would be unsuited for manufacture from an economically disposable, non-metallic material due to the various provisions for threaded mechanical fasteners, such as set screws, which necessarily require a relatively hard material for durability. While claims are made for various types of needles, no improvement is claimed for securing the associated needle bar within the actuating mechanism.

Typically, the needle bars associated with such devices are similar to that disclosed in Yacowitz U.S. Patent No. 4,771,660. The needle bar disclosed in this patent contains a loop formed integrally of the same material as that of the remainder of the needle bar. Such a loop allows relatively loose tolerances and fails to provide any cushioning effect for the direct metal to metal contact of the needle bar loop and actuating mechanism.

SUMMARY OF THE INVENTION

Accordingly, it is an object of the present invention to provide tattooing equipment which is economical to manufacture.

It is another object of the present invention to provide tattoo equipment which may be readily disposed of after a single use.

It is an additional object of the present invention to provide tattoo equipment at least a portion of which is of a material which causes it to be incapable of withstanding the heat and pressure normally associated with the sterilization process used for such equipment, and which therefore must be discarded.

It is a further object of the present invention to provide tattoo equipment which is completely sealed before use and which seals must be broken in order to be used, thereby making obvious the fact of prior use and alerting persons of the need for disposal.

Still another object of the present invention is to provide tattoo equipment which in combination with the above objects may make use of existing needle bars and needles currently manufactured, as well as those incorporated with the present invention.

An additional object of the present invention is to provide a needle holder which not only serves as a portion of the sterile container for the needle and needle bar, but is also readily adaptable to standard electrical actuating equipment.

Another object of the present invention is to provide improved tattoo needle bars and needles which are relatively simple and economical to manufacture.

With these and other objects in view which will more readily appear as the nature of the invention is better understood, the invention consists in the novel combinations and arrangement of parts hereinafter more fully described, illustrated and claimed with reference being made to the attached drawings.

BRIEF DESCRIPTION OF THE DRAWINGS

Similar reference characters designate corresponding parts throughout the several figures of the drawings.

DESCRIPTION OF THE PREFERRED EMBODIMENT

Figure 1:
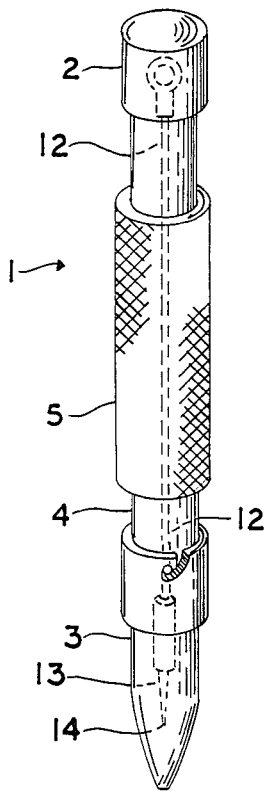
FIG. 1 is a perspective view of the needle holder and caps in their closed, sealed state.

Referring now to the drawings, the present invention will be understood to relate to an improvement in tattoo equipment, particularly relating to the sanitation of such equipment. FIG. 1 of the drawings discloses a sealed container 1, insuring that the needle 13 or 13a and needle bar assembly 12 enclosed therein remain in a sterile condition until container 1 is opened. Non-metallic components of container 1, which consist of upper cap 2, lower cap 3, and needle holder tube 4, are preferably formed of a plastic material for ease and economy of manufacture, which allows disposability of the apparatus after a single use. Components comprising container 1 may be formed of a material with a sufficiently low melting point so as to preclude sterilization by means of very high temperature and pressure, thus requiring its disposal and precluding more than a single use.

Upper cap 2 and lower cap 3 are mechanically or otherwise secured to needle holder tube 4, which serves as a portion of container 1 before caps 2 and 3 are removed. Following the removal of caps 2 and 3, needle holder tube 4 containing needle 13 or 13a and needle bar assembly 12 may be installed in a standard electrical tattooing device, not shown, for use as the standard needle holder and grip for applying the tattoo.

Figure 2:
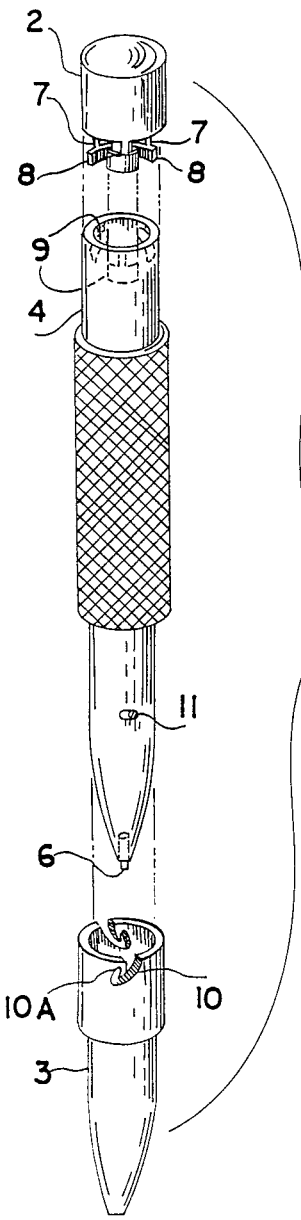
FIG. 2 is an exploded perspective view of the assembly.

Needle holder tube 4 is provided with various features to enable it to be suitable for such purpose. The portion 5 of tube 4 used as a grip during the application of a tattoo is knurled or otherwise roughened to provide a surface of relatively high friction coefficient, and a tubular tip 6, better shown in FIG. 2, is preferably formed of stainless steel for durability and sanitation. Such a tip 6 may be fashioned for different types of needles 13 or 13a used in the tattooing art. In general, tube 4 is formed in a size and shape suitable for use as a tattoo needle bar holder for the application of tattoos.

FIG. 2 also discloses further detail relative to the securing mechanism for upper and lower caps 2 and 3. Upper cap 2 contains a plurality of frangible extensions 7 with widened portions 8, which engage mating receptacles 9 within the upper portion of tube 4 upon assembly, thereby containing needle 13 or 13a and needle bar assembly 12 within tube 4. Lower cap 3 consists of a completely enclosed extension in order to fully protect needle tip 14 or 14a of the needle bar assembly 12 as the assembly 12 is enclosed within sealed container 1. Lower cap 3 is equipped with a plurality of slots 10 which are fashioned to engage pins 11 on the lower portion of tube 4, thus retaining needle bar assembly 12 securely within the assembled container 1 in a sanitary manner. Such slots 10 of cap 3 and pins 11 of holder 4 are preferably fashioned in such a way as to permanently damage pins 11, thereby causing cap 3 to be incapable of being reinstalled upon holder 4 and alerting potential users of the equipment of its prior use. This may be done by forming slots 10 with a relatively shallow slope so as to engage pins 11 gradually, and then forming upward portion 10a at the end of slot 10 to securely hold pins 11 of tube 4. In this way, cap 3 cannot be removed once installed without permanently damaging pins 11 and thereby precluding reassembly.

Figure 3:
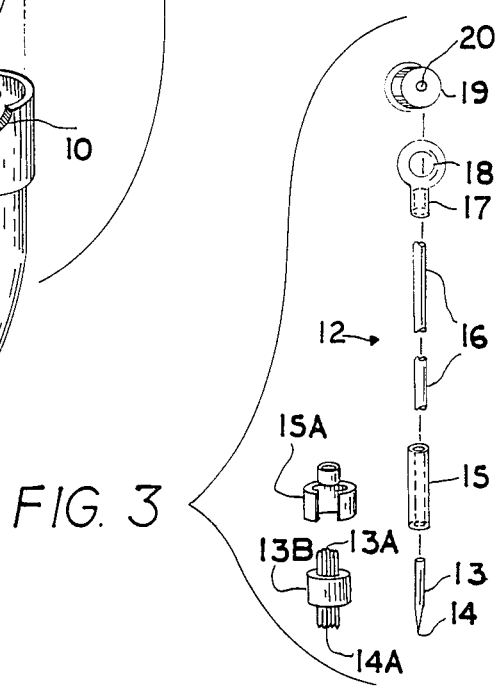
FIG. 3 is an exploded detail of a needle bar and typical needles.

Needle bar assembly 12 shown in FIG. 3 comprises several components which upon assembly are installed within container 1. Needle 13 or 13a is preferably formed of stainless steel, as are all other metallic components of the device, and may be formed as a "liner" needle 13 with a single tip 14, or as a "shader" needle 13a comprising a plurality of relatively fine tips 14a. Such a plurality of needle tips 14a comprising a "shader" needle 13a may be retained as an assembly by means of a band 13b or like device. Needle 13 or 13a may then be secured to needle bar 16 by means of lower ferrule 15 in the case of "liner" needle 13, or ferrule 15a in the case of "shader" needle 13a.

Needle bar 16 is fitted with an upper ferrule 17 at its end opposite that of needles 13 or 13a. Upper ferrule 17 contains an eye 18 into which an elastomer grommet 19 may be inserted. Grommet 19 contains a smaller eye 20, and thus provides a relatively precise fit between needle bar 16 and upper ferrule 17 and the operating mechanism of a tattoo apparatus, not shown. Each of the metallic components of needle bar assembly 12 may be secured together by crimping, silver solder, or other means.

During manufacture each component of the invention is sterilized, and needle bar assembly 12 is placed within tube 4 in a manner allowing needle tip 14 or 14a to protrude from tubualr tip 6, which is properly fashioned to accept either a "liner" needle 13 or a "shader" needle 13a. Needle bar assembly 12 is prevented from passing through tubular tip 6 due to the relatively large diameter of ferrule 15 or 15a, and further protected in a sanitary manner by the installation of lower cap 3 which is assembled to tube 4 by means of pins 11 engaging slots 10 of lower cap 3 and becoming locked into place within portions 10a of slots 10. Upper cap 2 is fitted in place over upper ferrule 17 of needle assembly 12 contained within tube 4 by means of widened portions 8 of extensions 7 of upper cap 2 engaging mating receptacles 9 within tube 4. To further insure the sterility of the assembly it may of course be sealed within a container of plastic or other suitable material in a manner well known in the art.

In order to use the device, any packaging is of course removed and upper cap 2 is removed from tube 4 by breaking frangible extensions 7, thereby exposing eye 18 and grommet 19 of needle bar assembly 12. Holder 4 and eye 20 of grommet 19 of needle bar assembly 12 may then be assembled with a standard electrical tattoo mechanism, lower cap 3 removed, and the device is then ready for use.

After use, the relatively low cost of needle holder tube 4 in its preferred embodiment of plastic material allows the economical disposal of the device. Needle assembly 12, comprising relatively inexpensive parts rather than a few intricately machined components, is also economically disposable. Further, by forming such non - metallic parts as upper and lower caps 2 and 3, tube 4, and grommet 19 of a plastic or elastomer material of relatively low melting point, any attempt to sterilize the apparatus for further use will lead to damage to the above plastic or elastomer components thereby rendering them unusable for further use. In addition, the standard inks or dyes commmonly used in the tattooing art will tend to stain the plastic materials used, thus providing obvious notice that the device has been used and should therefore be discarded.

It is to be understood that the present invention is not limited to the sole embodiment described above, but encompasses any and all embodiments within the scope of the following claims.

I claim:

1. A disposable tattoo needle assembly and needle bar holder comprising;
   a tubular needle bar holder,
   an upper and a lower cap sealing the upper and lower ends respectively of said holder, and
   a tattoo needle assembly contained therein.

2. A disposable tattoo needle assembly and needle bar holder according to claim 1 wherein:
   one or more of said protective caps are frangibly attached to said needle bar holder so as to cause permanent damage to said caps or said holder upon removal of said caps from said holder, thereby rendering said caps incapable of reinstallation upon said holder.

3. A disposable tattoo needle assembly and needle bar holder according to claim 1 wherein;
   said needle bar holder is formed of a material incapable of withstanding the temperatures and pressures associated with sterilization methods such as autoclaving, which attempt at sterilization would render said holder incapable of further use.

4. A disposable tattoo needle assembly and needle bar holder according to claim 1 wherein;
   said needle bar holder is formed of a material readily discolored by the inks and dyes commonly used in the tattoo industry, thereby providing notice of use after such use has occurred.

5. A disposable tattoo needle assembly and needle bar holder according to claim 1 wherein;
said needle bar holder contains a tip fashioned to properly fit a given type of tattoo needle, depending upon the type of needle to be installed within said needle bar holder at the time of manufacture.

6. A disposable tattoo needle assembly and needle bar holder according to claim 1 wherein;
said assembly contains a needle bar formed of a length of round metallic rod, and
said needle bar contains a ferrule formed as a separate component attached to said needle bar.

7. A disposable tattoo needle assembly and needle bar holder according to claim 6 wherein;
said ferrule contains an eye, and
said eye is fitted with a grommet, whereby said grommet may provide a precise fit to a tattoo apparatus actuating mechanism, thereby providing smooth operation of said needle bar.

8. A disposable tattoo needle assembly and needle bar holder according to claim 7 wherein;
said grommet is formed of a material incapable of withstanding the temperatures and pressures associated with sterilization methods such as autoclaving, which attempt at sterilization would render said grommet incapable of further use.

* * * * *